(12) United States Patent
Amemiya

(10) Patent No.: US 6,868,729 B2
(45) Date of Patent: Mar. 22, 2005

(54) METHOD OF DRIVING TWO-DIMENSIONAL ARRAY ULTRASONIC PROBE, AND ULTRASONIC DIAGNOSTIC APPARATUS

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/400,608

(22) Filed: Mar. 27, 2003

(65) Prior Publication Data
US 2003/0188582 A1 Oct. 9, 2003

(30) Foreign Application Priority Data
Mar. 29, 2002 (JP) .................................. 2002-093911

(51) Int. Cl.[7] .............................................. G01N 29/24
(52) U.S. Cl. ............................ 73/626; 73/628; 600/447
(58) Field of Search .......................... 73/624, 625, 626, 73/627, 628, 641, 642; 600/440, 441, 443, 444, 446, 447

(56) References Cited

U.S. PATENT DOCUMENTS

| | | | | |
|---|---|---|---|---|
| 4,140,022 A | * | 2/1979 | Maslak .......................... | 73/626 |
| 4,204,435 A | * | 5/1980 | Bridoux et al. ................ | 73/626 |
| 4,307,613 A | * | 12/1981 | Fox ............................... | 73/626 |
| 4,580,451 A | * | 4/1986 | Miwa et al. .................... | 73/626 |
| 5,229,933 A | * | 7/1993 | Larson, III ................... | 600/459 |
| 5,638,821 A | * | 6/1997 | Nakamura et al. ........... | 600/447 |
| 5,860,931 A | | 1/1999 | Chandler | |
| 5,922,962 A | | 7/1999 | Ishrak et al. | |
| 5,997,479 A | * | 12/1999 | Savord et al. ............... | 600/447 |
| 6,464,638 B1 | | 10/2002 | Adams et al. | |
| 6,508,764 B1 | * | 1/2003 | Thiele et al. ................ | 600/437 |
| 6,736,779 B1 | * | 5/2004 | Sano et al. ................... | 600/447 |

FOREIGN PATENT DOCUMENTS

| | | | | |
|---|---|---|---|---|
| EP | 1214909 A1 | * | 6/2002 | ............ A61B/8/00 |
| WO | WO 01/21072 A1 | * | 3/2001 | ............ A61B/8/00 |

* cited by examiner

Primary Examiner—Hezron Williams
Assistant Examiner—Rose M. Miller
(74) Attorney, Agent, or Firm—Carl B. Horton, Esq.; Armstrong Teasdale LLP

(57) ABSTRACT

For the purpose of reducing the load on hardware for driving a two-dimensional array ultrasonic probe having a multiplicity of transducers, an ultrasonic diagnostic apparatus includes programmable gain amplifiers a00–a99 for amplifying signal voltages e00–e99 from transducers in a two-dimensional array ultrasonic probe, voltage-to-current converters h00–h99 for converting the voltages into current signals i00–i99, a matrix switch M for outputting additive current signals I0–I9 obtained by dividing the current signals i00–i99 into groups and adding current signals in respective groups, current-to-voltage converters H0–H9 for converting the currents into voltage signals, programmable gain amplifiers A0–A9, A–D converters C0–C9, and a digital beamformer unit B for conducting reception beamforming using digital signals D0–D9 and outputting an acoustic line signal W.

7 Claims, 14 Drawing Sheets

METHOD OF DRIVING TWO-DIMENSIONAL ARRAY ULTRASONIC PROBE, AND ULTRASONIC DIAGNOSTIC APPARATUS

CROSS REFERENCE TO RELATED APPLICATIONS

This application claims the benefit of Japanese Application No. 2002-093911 filed Mar. 29, 2002.

BACKGROUND OF THE INVENTION

The present invention relates to a method of driving a two-dimensional array ultrasonic probe, and an ultrasonic diagnostic apparatus, and more particularly to a method of driving a two-dimensional array ultrasonic probe, and an ultrasonic diagnostic apparatus that can reduce the load on hardware for driving the two-dimensional array ultrasonic probe.

In a conventional ultrasonic probe having transducers arranged in one dimension, the number of the transducers is, for example, about 128. Therefore, the hardware for driving the ultrasonic probe has the capacity to drive about 128 transducers.

In recent years, a two-dimensional array ultrasonic probe having transducers arranged in two dimensions has been developed, in which, for example, the number of transducers is 1024 when the transducers are arranged in a 32 by 32 matrix. Therefore, the hardware for driving the two-dimensional array ultrasonic probe is required to have the capacity to drive as many as 1024 transducers.

However, if hardware must have the capacity to drive as many as 1024 transducers, the load on the hardware becomes very large.

SUMMARY OF THE INVENTION

It is therefore an object of the present invention to provide a method of driving a two-dimensional array ultrasonic probe, and an ultrasonic diagnostic apparatus that can reduce the load on hardware for driving the two-dimensional array ultrasonic probe.

In a first aspect, the present invention provides a method of driving a two-dimensional array ultrasonic probe, characterized in comprising: dividing N transducers in the two-dimensional array ultrasonic probe into Z (<N) groups, in which transducers lying at the same or approximately the same distance from a focal spot of an ultrasonic beam are in the same group; and driving the transducers on a group-by-group basis.

Since transducers lying at the same or approximately the same distance from a focal spot of an ultrasonic beam receive an ultrasonic echo spherically propagating from the focal spot at the same or approximately the same time, the received echo may be added to form one received signal. Also in transmission, transducers lying at the same or approximately the same distance from a focal spot of an ultrasonic beam may be excited by one transmission signal by the same reason.

Therefore, according to the method of driving a two-dimensional array ultrasonic probe of the first aspect, transducers lying at the same or approximately the same distance from a focal spot of an ultrasonic beam are grouped together, and the transducers are driven on a group-by-group basis. Thus, hardware capable of driving transducers in a number of groups less than the number of transducers in the two-dimensional array ultrasonic probe works sufficiently, thus reducing the load on hardware for driving the two-dimensional array ultrasonic probe.

In a second aspect, the present invention provides a method of driving a two-dimensional array ultrasonic probe, characterized in comprising: dividing N transducers in the two-dimensional array ultrasonic probe into Z (<N) groups, in which transducers lying at the same or approximately the same distance from an imaginary focal spot defined by projecting a focal spot of an ultrasonic beam onto an imaginary plane containing a reception surface of the two-dimensional array ultrasonic probe are in the same group; and driving the transducers on a group-by-group basis.

A line on which a sphere of an ultrasonic echo propagating from a focal spot of an ultrasonic beam intersects an imaginary plane containing a reception surface of a two-dimensional array ultrasonic probe forms a circle with a center at an imaginary focal spot defined by projecting the focal spot onto the imaginary plane. Therefore, transducers lying at the same or approximately the same distance from the imaginary focal spot are exactly the same as those lying at the same or approximately the same distance from the focal spot.

Therefore, the method of driving a two-dimensional array ultrasonic probe of the second aspect gives the same result as that in the method of driving a two-dimensional array ultrasonic probe of the first aspect, thus reducing the load on hardware for driving the two-dimensional array ultrasonic probe. Moreover, processing for finding transducers lying at the same or approximately the same distance from an imaginary focal spot is simpler than that of finding transducers lying at the same or approximately the same distance from a focal spot.

In a third aspect, the present invention provides the method of driving a two-dimensional array ultrasonic probe having the aforementioned configuration, characterized in that $4096 \geq N \geq 256$.

According to the method of driving a two-dimensional array ultrasonic probe of the third aspect, since the number of transducers N in a two-dimensional array ultrasonic probe is $4096 \geq N \geq 256$, a two-dimensional array of 64×64–16×16 or of 32×128–8×32 can be employed.

In a fourth aspect, the present invention provides the method of driving a two-dimensional array ultrasonic probe having the aforementioned configuration, characterized in that $128 \geq Z \geq 32$.

According to the method of driving a two-dimensional array ultrasonic probe of the fourth aspect, since the number of groups is $128 \geq Z \geq 32$, the load on hardware for driving the two-dimensional array ultrasonic probe is reduced.

In a fifth aspect, the present invention provides an ultrasonic diagnostic apparatus characterized in comprising: N voltage amplifiers for amplifying signal voltages from transducers in a two-dimensional array ultrasonic probe; N voltage-to-current converters for converting voltages output from said voltage amplifiers into current signals; a current addition circuit having N inputs supplied with said current signals, and having Z (<N) outputs for outputting additive current signals obtained by dividing the N inputs into Z (<N) groups and adding current signals in respective groups; Z current-to-voltage converters for converting said additive current signals into voltage signals; and a beamformer for conducting reception beamforming using said voltage signals.

According to the ultrasonic diagnostic apparatus of the fifth aspect, the methods of driving a two-dimensional array ultrasonic probe can be suitably implemented. Moreover, since addition is performed on current signals, the frequency characteristic is not degraded even if the length of wiring increases to some degree.

In a sixth aspect, the present invention provides the ultrasonic diagnostic apparatus having the aforementioned configuration, characterized in that said current addition circuit is a matrix switch.

Since the ultrasonic diagnostic apparatus of the sixth aspect employs a matrix switch, the group arrangement can be dynamically modified according to the change of the focal spot.

In a seventh aspect, the present invention provides the ultrasonic diagnostic apparatus having the aforementioned configuration, characterized in that said beamformer forms a received beam in one direction, and said current addition circuit arranges inputs corresponding to transducers lying at the same or approximately the same distance from a focal spot of said received beam into the same group.

According to the ultrasonic diagnostic apparatus of the seventh aspect, the methods of driving a two-dimensional array ultrasonic probe can be suitably implemented.

In an eighth aspect, the present invention provides the ultrasonic diagnostic apparatus having the aforementioned configuration, characterized in that said beamformer forms received beams in a plurality of directions such that imaginary focal spots thereof defined by projecting respective focal spots onto an imaginary plane containing a reception surface of the two-dimensional array ultrasonic probe overlie one another at the same position, and said current addition circuit arranges inputs corresponding to transducers lying at the same or approximately the same distance from said imaginary focal spots into the same group.

Transducers in a two-dimensional array ultrasonic probe are divided into groups, in which transducers lying at the same or approximately the same distance from a focal spot of an ultrasonic beam are in the same group. On the other hand, the transducers in the two-dimensional array ultrasonic probe are divided into groups, in which transducers lying at the same or approximately the same distance from an imaginary focal spot defined by projecting the focal spot onto an imaginary plane containing a reception surface of the two-dimensional array ultrasonic probe are in the same group. These groups coincide with each other.

Next, considering a plurality of focal spots at different positions, the transducers in the two-dimensional array ultrasonic probe are divided into groups corresponding to the focal spots, in which transducers lying at the same or approximately the same distance from each focal spot are in the same group. If imaginary focal spots defined by projecting the plurality of the focal spots onto an imaginary plane containing a reception surface of the two-dimensional array ultrasonic probe overlie one another, all the groups coincide with one another.

Therefore, according to the ultrasonic diagnostic apparatus of the eighth aspect, one current addition circuit can be used in common even if the beamformer forms received beams in a plurality of directions.

In a ninth aspect, the present invention provides an ultrasonic diagnostic apparatus characterized in comprising: N voltage amplifiers for amplifying signal voltages from transducers in a two-dimensional array ultrasonic probe; N multiplied by k ($k \geq 2$) voltage-to-current converters for converting voltages output from said voltage amplifiers into current signals; k current addition circuits each having N inputs supplied with said current signals, and having Z (<N) outputs for outputting additive current signals obtained by dividing the N inputs into Z (<N) groups and adding current signals in respective groups; Z multiplied by k current-to-voltage converters for converting said additive current signals into voltage signals; and k beamformers for conducting reception beamforming using said voltage signals.

Since the ultrasonic diagnostic apparatus of the ninth aspect comprises respective voltage-to-current converters and the like corresponding to received beams in k directions, the beamformers can form received beams in the k directions without limitation on the position of the focal spot.

In a tenth aspect, the present invention provides the ultrasonic diagnostic apparatus having the aforementioned configuration, characterized in that said current addition circuits are matrix switches.

Since the ultrasonic diagnostic apparatus of the tenth aspect employs matrix switches, the group arrangement can be dynamically modified according to the change of the focal spot.

In an eleventh aspect, the present invention provides the ultrasonic diagnostic apparatus having the aforementioned configuration, characterized in that said k beamformers form received beams in one direction having respective focal spots of different depths, and said k current addition circuits arrange inputs corresponding to transducers lying at the same or approximately the same distance from each focal spot into the same group; and said ultrasonic diagnostic apparatus further comprises a combination circuit for combining the outputs from said k beamformers.

According to the ultrasonic diagnostic apparatus of the eleventh aspect, up to k focal spots of different depths can be defined in received beams in one direction.

In a twelfth aspect, the present invention provides the ultrasonic diagnostic apparatus having the aforementioned configuration, characterized in that said combination circuit is for adding the outputs from the k beamformers with weights corresponding to the depth.

According to the ultrasonic diagnostic apparatus of the twelfth aspect, outputs obtained from received beams corresponding to focal spots of different depths can be smoothly combined.

In a thirteenth aspect, the present invention provides the ultrasonic diagnostic apparatus having the aforementioned configuration, characterized in that said k beamformers form received beams in different directions having respective focal spots of different depths, and said current addition circuits arrange inputs corresponding to transducers lying at the same or approximately the same distance from each focal spot into the same group.

The ultrasonic diagnostic apparatus of the thirteenth aspect can conduct scanning with received beams in k separate directions.

In a fourteenth aspect, the present invention provides the ultrasonic diagnostic apparatus having the aforementioned configuration, characterized in that said voltage amplifiers are programmable gain amplifiers.

The ultrasonic diagnostic apparatus of the fourteenth aspect can apply TGC (time gain control) when amplifying signal voltages from the transducers in the two-dimensional array ultrasonic probe for the first time.

In a fifteenth aspect, the present invention provides the ultrasonic diagnostic apparatus having the aforementioned configuration, characterized in that programmable gain amplifiers are provided between said current-to-voltage converters and said beamformer.

The ultrasonic diagnostic apparatus of the fifteenth aspect can apply TGC using a smaller number of programmable gain amplifiers.

In a sixteenth aspect, the present invention provides the ultrasonic diagnostic apparatus having the aforementioned configuration, characterized in that $4096 \geq N \geq 256$.

According to the ultrasonic diagnostic apparatus in the sixteenth aspect, since the number of transducers N in the two-dimensional array ultrasonic probe is $4096 \geq N \geq 256$, a two-dimensional array of 64×64–16×16 or of 32×128–8×32 can be employed.

In a seventeenth aspect, the present invention provides the ultrasonic diagnostic apparatus as defined by any one of claims 5–16 having the aforementioned configuration, characterized in that $128 \geq Z \geq 32$.

According to the ultrasonic diagnostic apparatus in the seventeenth aspect, since the number of groups Z is $128 \geq Z \geq 32$, the load on hardware for driving the two-dimensional array ultrasonic probe is reduced.

According to the method of driving a two-dimensional array ultrasonic probe, and an ultrasonic diagnostic apparatus of the present invention, the load on hardware for driving a two-dimensional array ultrasonic probe having a multiplicity of transducers can be reduced.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to several embodiments shown in the accompanying drawings.

First Embodiment

Figure 1:
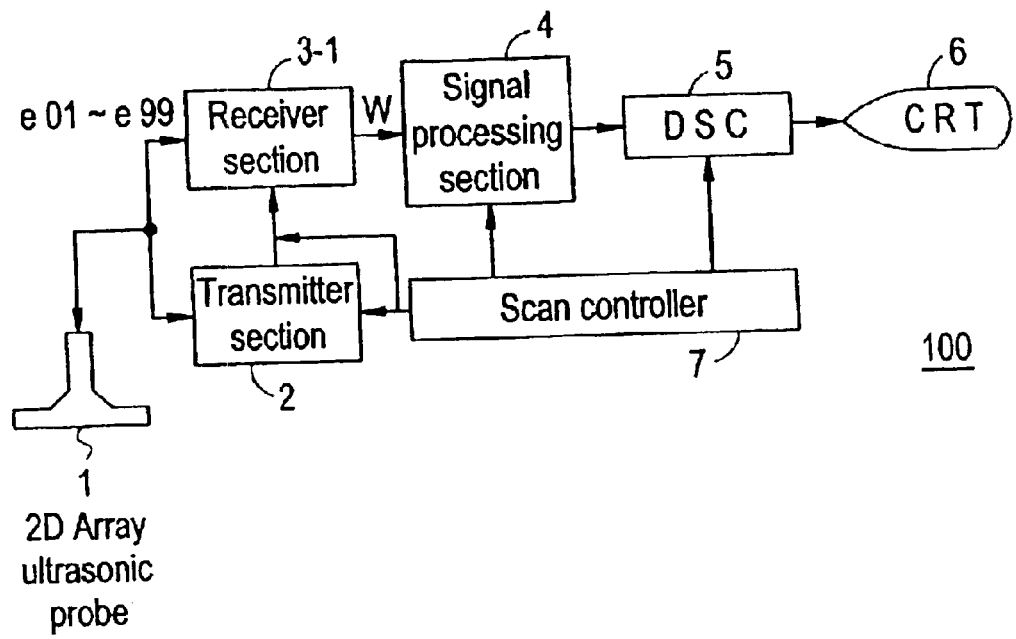
FIG. 1 is a configuration diagram showing an ultrasonic diagnostic apparatus in accordance with a first embodiment.

FIG. 1 is a configuration diagram of an ultrasonic diagnostic apparatus 100 in accordance with a first embodiment.

The ultrasonic diagnostic apparatus 100 comprises a two-dimensional array ultrasonic probe 1, a transmitter section 2 that excites transducers in the two-dimensional array ultrasonic probe 1 to transmit ultrasonic pulses in a desired beam transmission direction, a receiver section 3-1 for receiving ultrasonic echoes from a desired beam reception direction via the two-dimensional array ultrasonic probe and outputting an acoustic line signal W, a signal processing section 4 for processing the acoustic line signal W and outputting B-mode data etc., a DSC 5 for generating image data from the B-mode data etc., a CRT 6 for displaying an image etc. based on the image data, and a scan controller 7 for overall control.

Figure 4:
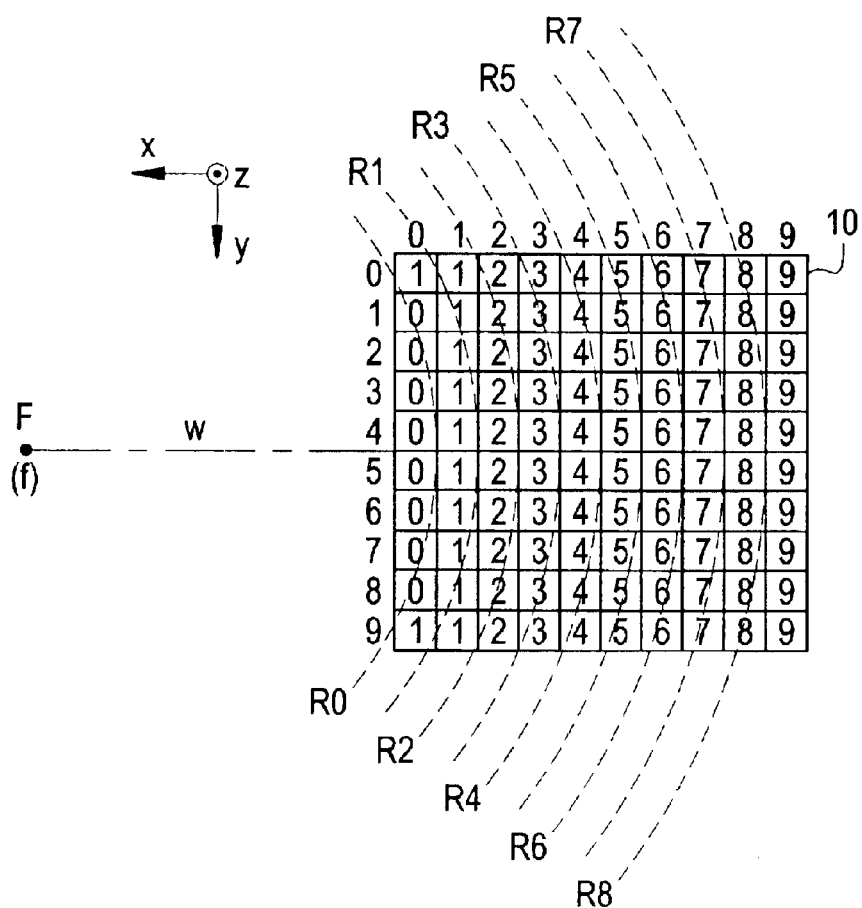
FIG. 4 is an explanatory diagram showing group arrangement of transducers in accordance with the first embodiment.

It is assumed that the two-dimensional array ultrasonic probe has an array of 10×10 transducers as shown in FIG. 4. The number 10×10 is selected for convenience of illustration, and in practice, the two-dimensional array has 64×64–16×16 or 32×128–8×32 transducers.

Figure 2:
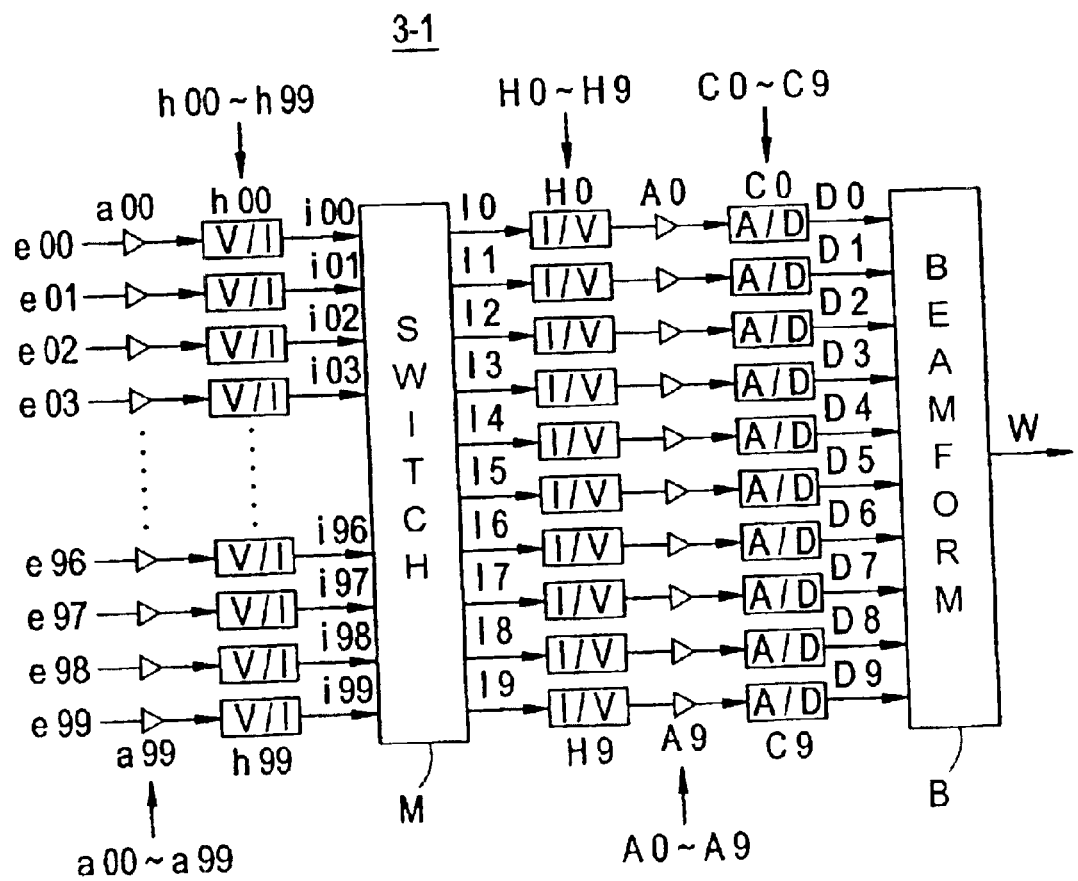
FIG. 2 is a detailed configuration diagram of a receiver section in accordance with the first embodiment.

FIG. 2 is a configuration block diagram of the receiver section 3-1. The receiver section 3-1 comprises one hundred programmable gain amplifiers a00–a99 for amplifying signal voltages e00–e99 from the transducers in the two-dimensional array ultrasonic probe 1, one hundred voltage-to-current converters h00–h99 for converting voltages output from the programmable gain amplifiers a00–a99 into current signals i00–i99, a matrix switch M having one hundred inputs supplied with the current signals i00–i99, and having ten outputs for outputting additive current signals I0–I9 obtained by dividing the one hundred inputs into ten groups and adding current signals in respective groups, ten current-to-voltage converters H0–H9 for converting the additive current signals I0–I9 into voltage signals, ten programmable gain amplifiers A0–A9 for amplifying the voltage signals, ten A–D converters C0–C9 for converting the amplified voltage signals into digital signals D0–D9, and a digital beamformer unit B for conducting reception beamforming using the digital signals D0–D9 and outputting an acoustic line signal W.

If either the programmable gain amplifiers a00–a99 or the programmable gain amplifiers A0–A9 apply TGC and the others do not, the ones that do not may be fixed-gain amplifiers.

Although the number of outputs in the matrix switch M is ten for convenience of illustration, it is more practical for the matrix switch M to have 128–32 outputs.

Figure 3:
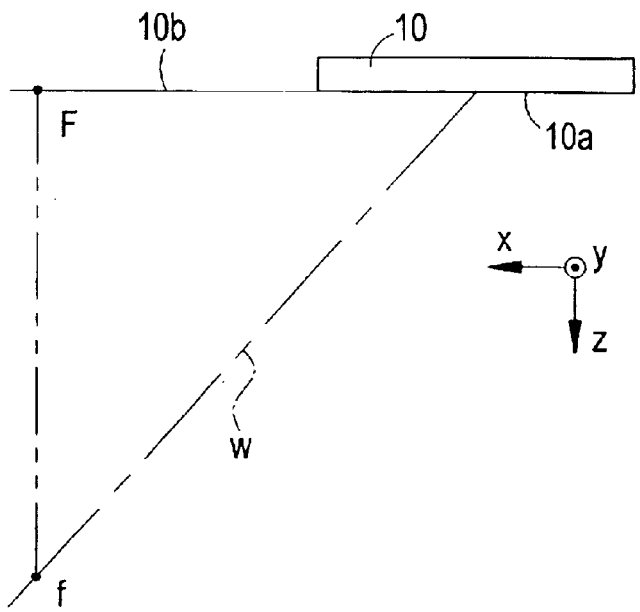
FIG. 3 is an explanatory diagram showing a received beam, focal spot and imaginary focal spot in accordance with the first embodiment.

Referring to FIG. 3, it is assumed that the beamformer unit B forms a received beam in a direction of a received beam centerline w having a focal spot f. Moreover, an imaginary focal spot F is defined as a point corresponding the focal spot f projected onto an imaginary plane 10b containing a reception surface 10a of the transducer array 10.

As shown in FIG. 4, the scan controller 7 divides the transducers in the transducer array 10 into ten groups, in which transducers lying at the same or approximately the same distance from the virtual focal spot F are in the same group. More particularly, the transducers are divided into ten groups based on arcs R0–R9 whose center is at the imaginary focal spot F. Such group arrangement is identical to that of putting transducers lying at the same or approximately the same distance from the focal spot f into the same group.

In FIG. 4, row/column indices of the transducers are marked outside the transducer array 10, and group indices "0"–"9" are marked at the positions of the transducers in the transducer array 10.

Specifically, the transducers 01–08 are assigned to a group index "0", the transducers 00, 09, and 10–19 are assigned to a group index "1", the transducers 20–29 are assigned to a group index "2", the transducers 30–39 are assigned to a group index "3", the transducers 40–49 are assigned to a group index "4", the transducers 50–59 are assigned to a group index "5", the transducers 60–69 are assigned to a group index "6", the transducers 70–79 are assigned to a group index "7", the transducers 80–89 are assigned to a group index "8", and the transducers 90–99 are assigned to a group index "9".

Next, the scan controller 7 divides the signal voltages e00–e99 into groups with group indices "0"–"9" corresponding to the group arrangement of the transducers, and accordingly divides the current signals i00–i99 into groups with group indices "0"–"9". The matrix switch M is then set so that it adds the current signals in respective groups and outputs the additive current signals I0–I9.

Figure 5:
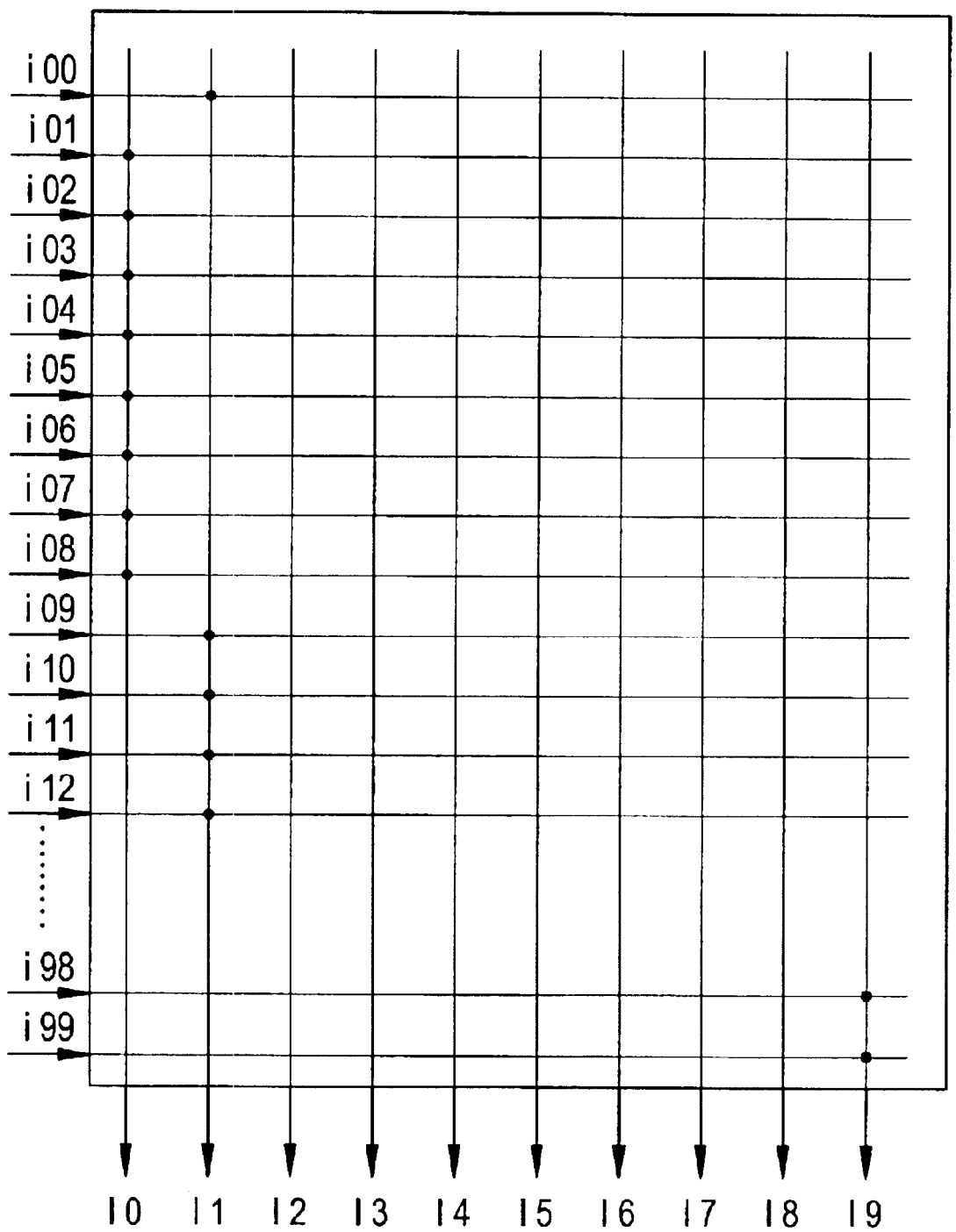
FIG. 5 is an explanatory diagram showing an example setting of a matrix switch in accordance with the first embodiment.

FIG. 5 shows part of the thus-set matrix switch.

An additive current signal I0 is a signal obtained by adding current signals i01–i08 assigned to the group index "0", an additive current signal I1 is a signal obtained by adding current signals i00, i09, i10–i19 assigned to the group index "1", an additive current signal I2 is a signal obtained by adding current signals i20–i29 assigned to the group index "2", an additive current signal I3 is a signal obtained by adding current signals i30–i39 assigned to the group index "3", an additive current signal I4 is a signal obtained by adding current signals i40–i49 assigned to the group index "4", an additive current signal I5 is a signal obtained by adding current signals i50–i59 assigned to the group index "5", an additive current signal I6 is a signal obtained by adding current signals i60–i69 assigned to the group index "6", an additive current signal I7 is a signal obtained by adding current signals i70–i79 assigned to the group index "7", an additive current signal I8 is a signal obtained by adding current signals i80–i89 assigned to the group index "8", and an additive current signal I9 is a signal obtained by adding current signals i90–i99 assigned to the group index "9".

Figure 6:
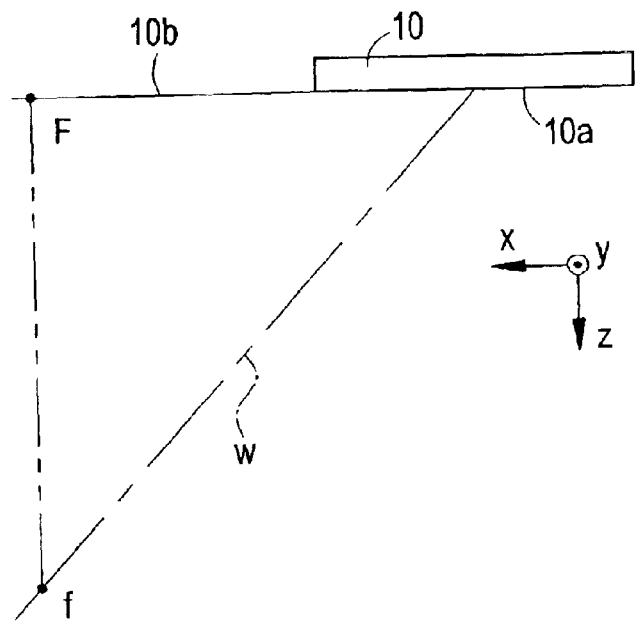
FIG. 6 is an explanatory diagram showing another received beam, focal spot and imaginary focal spot in accordance with the first embodiment.
Figure 7:
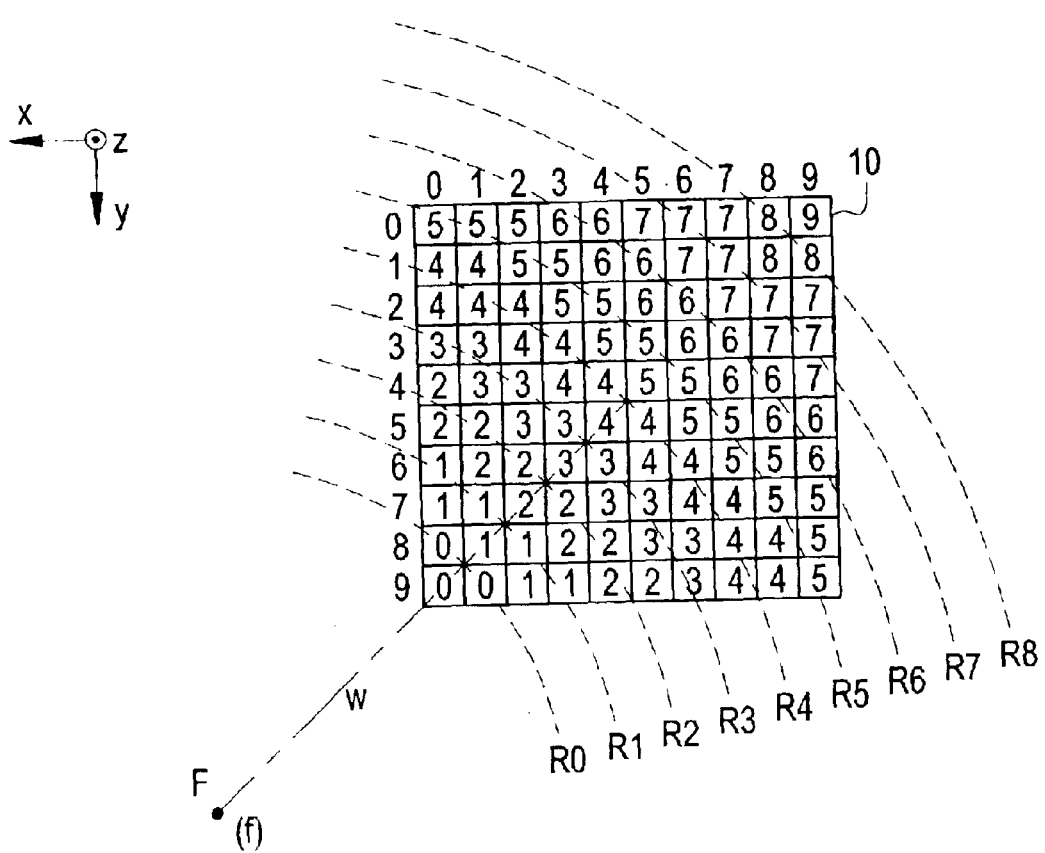
FIG. 7 is an explanatory diagram showing another example of group arrangement of transducers in accordance with the first embodiment.
Figure 8:
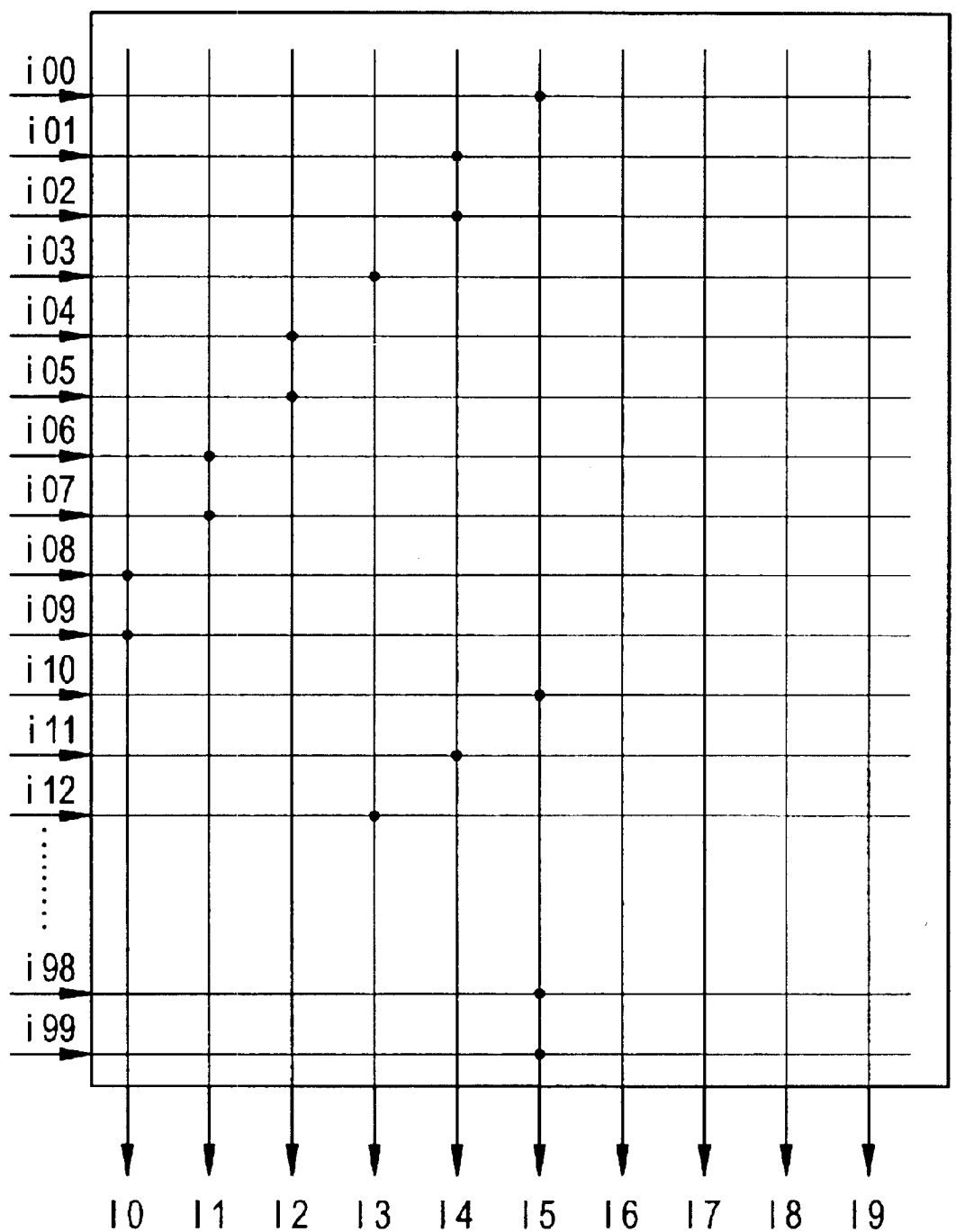
FIG. 8 is an explanatory diagram showing another example setting of the matrix switch in accordance with the first embodiment.

FIGS. 6 and 7 show another example of a received beam different from that of FIGS. 3 and 4. The transducers are divided into groups as shown in FIG. 7. The matrix switch M is set as shown in FIG. 8.

According to the ultrasonic diagnostic apparatus 100 of the first embodiment, the load on hardware for driving the two-dimensional array ultrasonic probe 1 that has many transducers can be reduced. Moreover, since current addition is employed, the frequency characteristic is not degraded even if the length of wiring increases to some degree.

Second Embodiment

Figure 9:
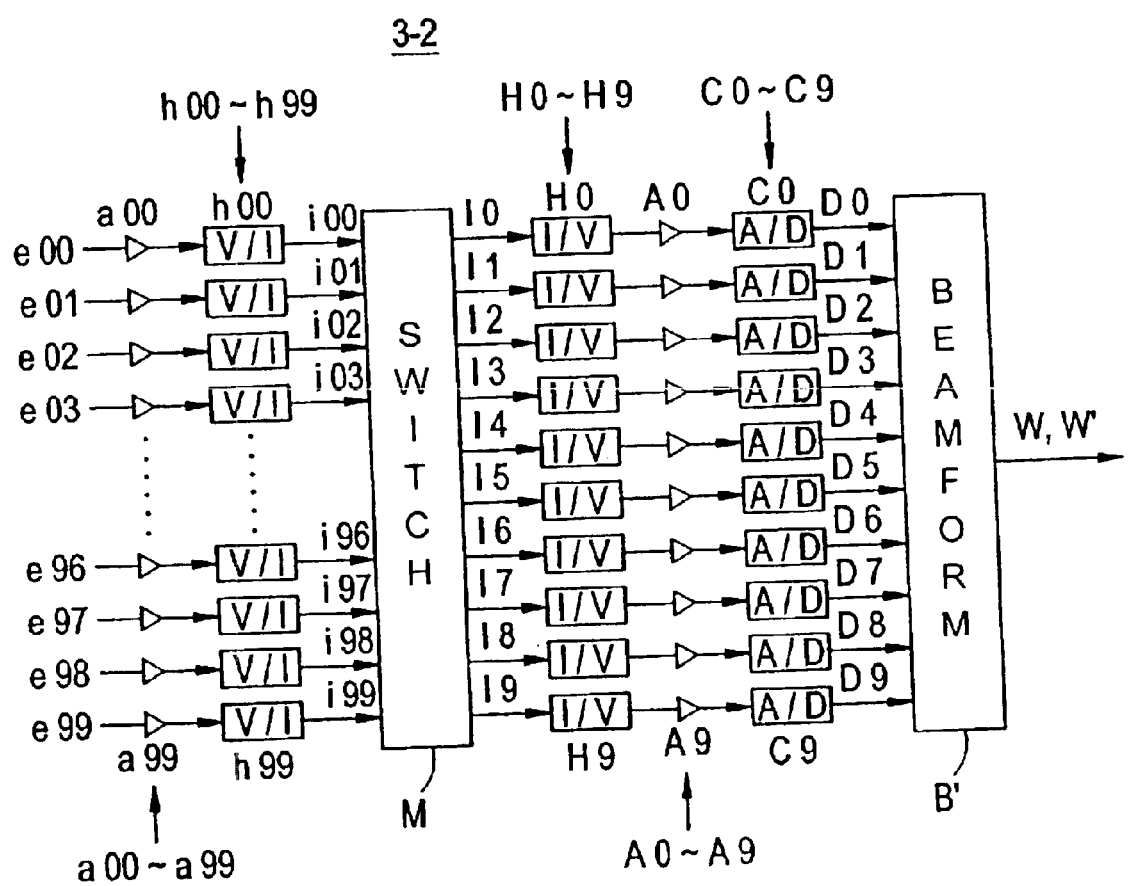
FIG. 9 is a detailed configuration diagram of a receiver section in accordance with a second embodiment.

An ultrasonic diagnostic apparatus of the second embodiment comprises a receiver section 3-2 shown in FIG. 9 in place of the receiver section 3-1 of FIG. 2.

The receiver section 3-2 comprises a digital beamformer B' in place of the digital beamformer unit B of FIG. 2.

Figure 10:
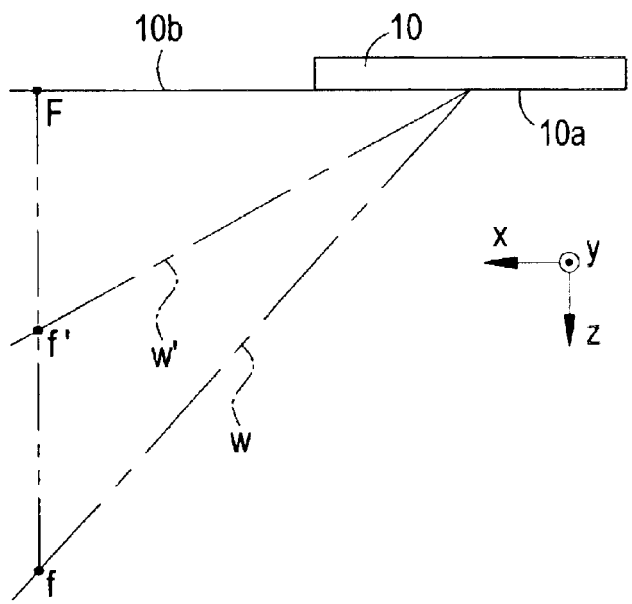
FIG. 10 is an explanatory diagram showing received beams, focal spots and imaginary focal spots in accordance with the second embodiment.
Figure 11:
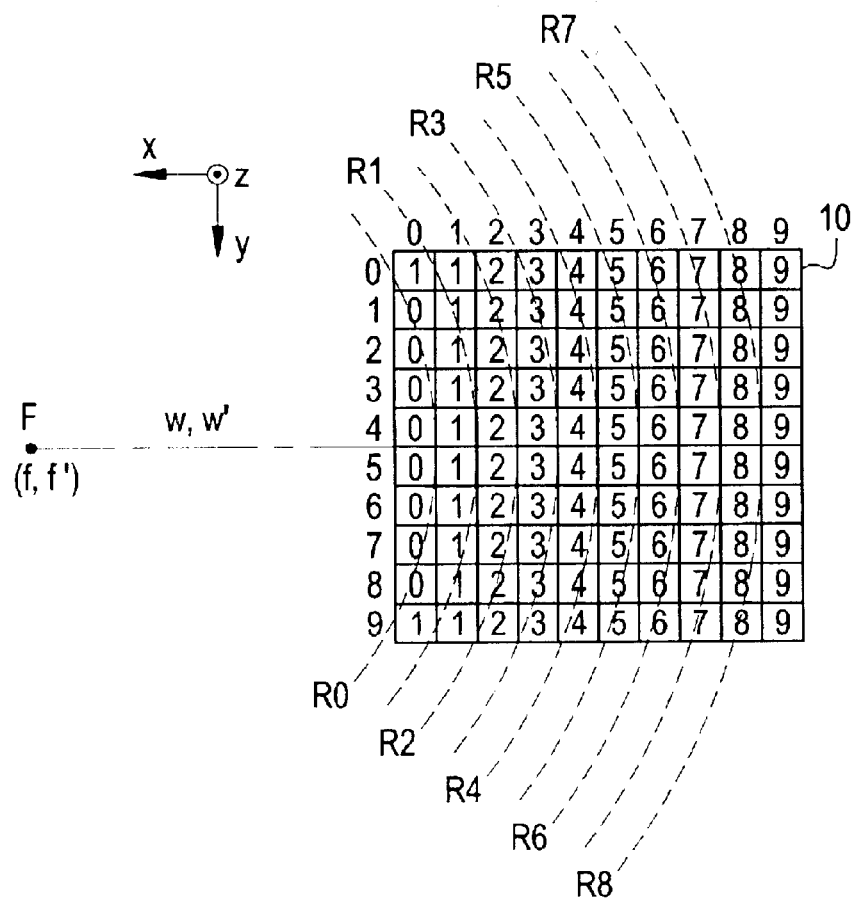
FIG. 11 is an explanatory diagram showing group arrangement of transducers in accordance with the second embodiment.

As shown in FIGS. 10 and 11, the digital beamformer unit B' forms received beams (w, w') in two directions having imaginary focal spots F and F defined by projecting respective focal spots f and f' onto an imaginary plane 10b, overlying each other at the same position.

When the imaginary focal spots F and F overlie each other at the same position as shown in FIG. 11, the transducers' group arrangement is the same even for the different received beams (w, w').

The matrix switch M can thus process the different received beams (w, w') in the same setting.

According to the ultrasonic diagnostic apparatus of the second embodiment, a plurality of ultrasonic beams can be simultaneously formed.

Third Embodiment

Figure 12:
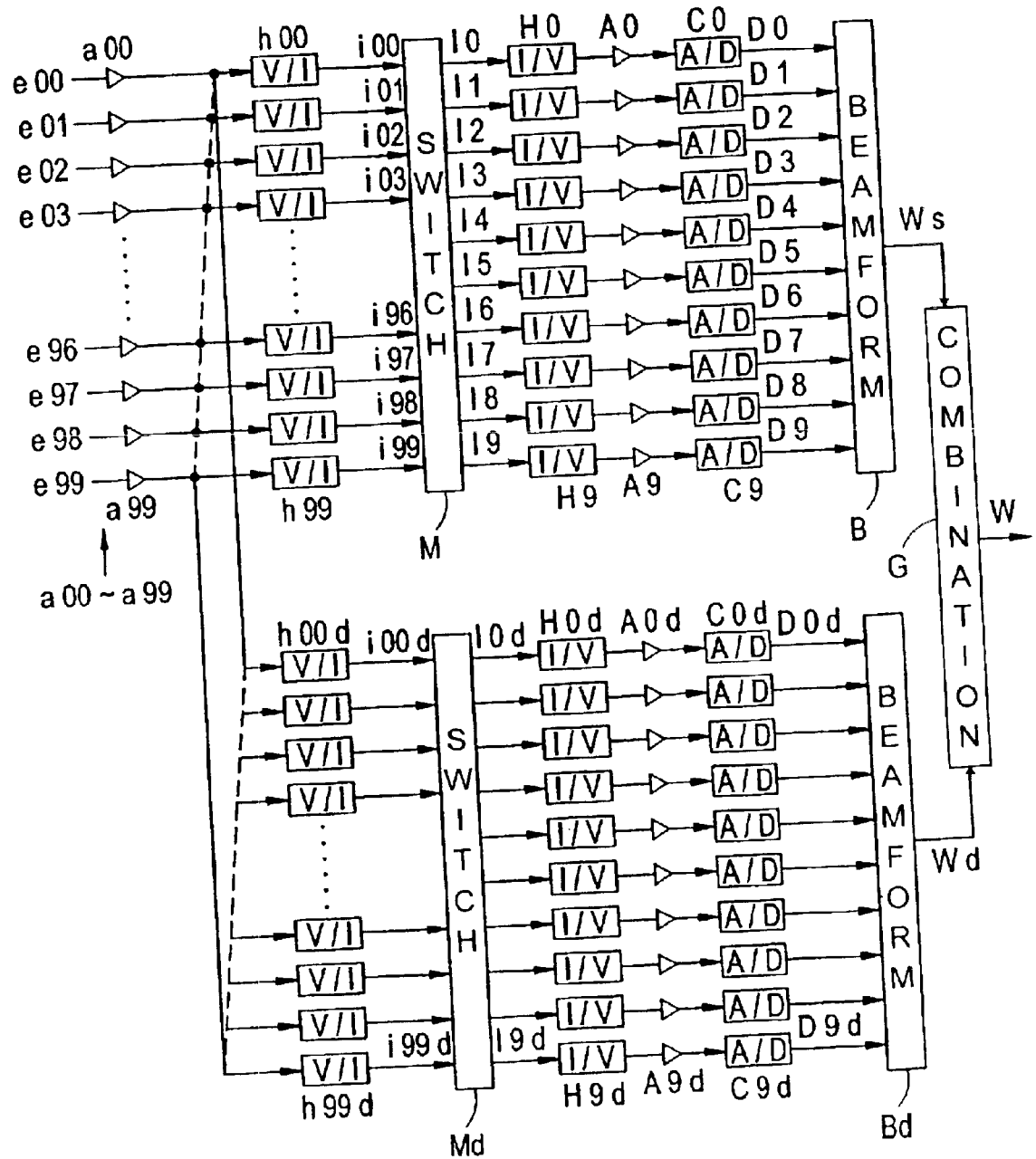
FIG. 12 is a detailed configuration diagram of a receiver section in accordance with a third embodiment.

An ultrasonic diagnostic apparatus of the third embodiment comprises a receiver section 3-3 shown in FIG. 12 in place of the receiver section 3-1 of FIG. 2.

The receiver section 3-3 comprises the configuration of the receiver section 3-1 of FIG. 2 additionally provided with another set of voltage-to-current converters h00d–h99d, a matrix switch Md, current-to-voltage converters H0d–H9d, programmable gain amplifiers A0d–A9d, A–D converters C0d–C9d, and a digital beamformer unit Bd, and in addition, a combination circuit G for combining an output Ws from the digital beamformer unit B and an output Wd from the digital beamformer unit Bd.

Figure 13:
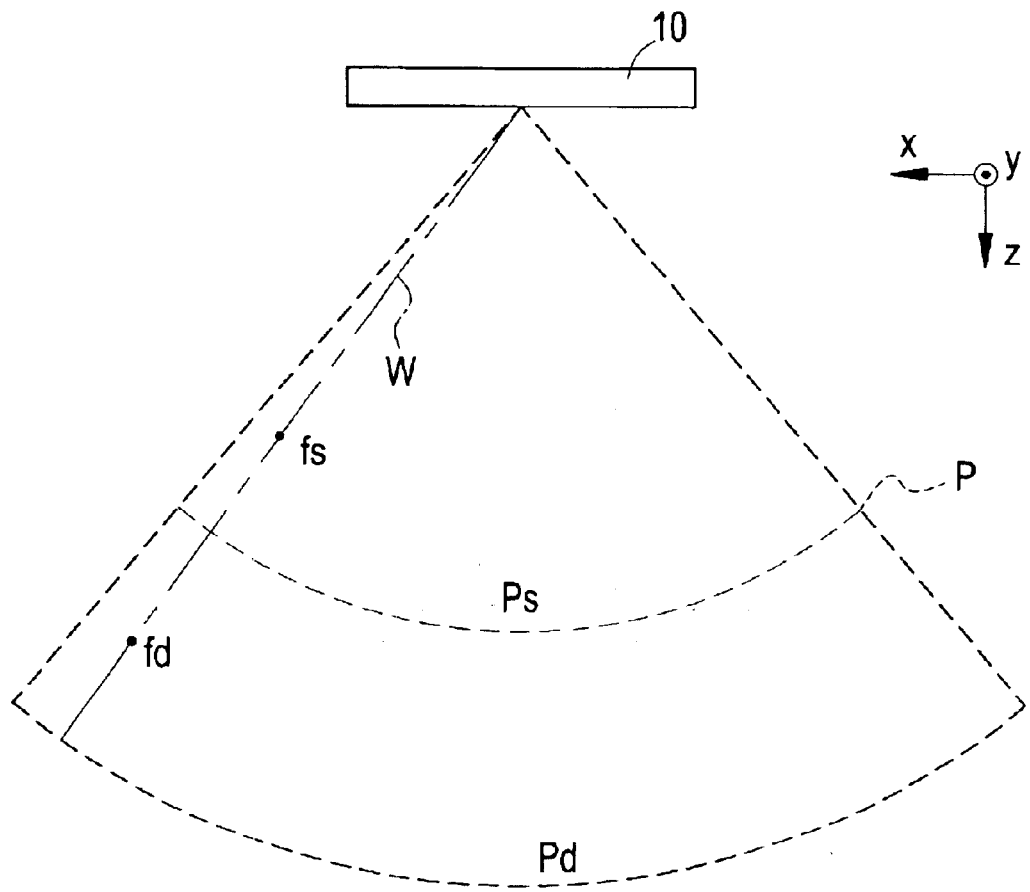
FIG. 13 is an explanatory diagram showing received beams, focal spots and a scan plane in accordance with the third embodiment.

As shown in FIG. 13, the digital beamformer unit B and the digital beamformer unit Bd form received beams (w) in the same direction. However, a shallow focal spot fs of the received beam (w) formed by the digital beamformer unit B is shallower than a deep focal spot fd of the received beam (w) formed by the digital beamformer unit Bd.

Figure 14:
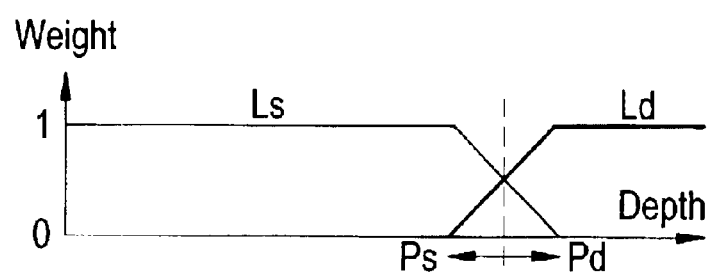
FIG. 14 is an explanatory diagram showing weights for addition in accordance with the third embodiment.

The combination circuit G adds the outputs Ws and Wd weighted using weights Ls and Ld shown in FIG. 14, as follows:

$$W = Ls \cdot Ws + Ld \cdot Wd.$$

Figure 15:
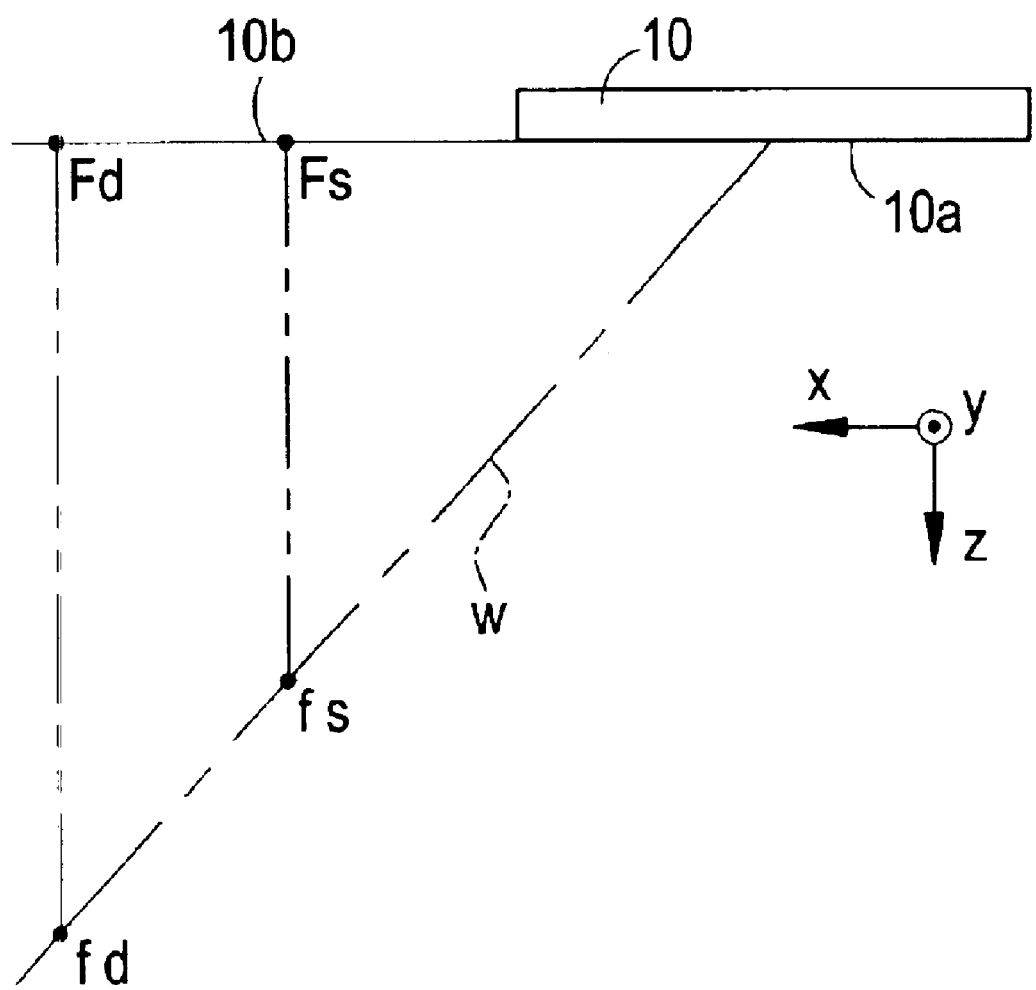
FIG. 15 is an explanatory diagram showing received beams, focal spots and imaginary focal spots in accordance with the third embodiment.

FIG. 15 shows a shallow imaginary focal spot Fs defined by projecting the shallow focal spot fs onto an imaginary plane 10b and a deep imaginary focal spot Fd defined by projecting the deep focal spot fd onto the imaginary plane 10b.

Figure 16A:
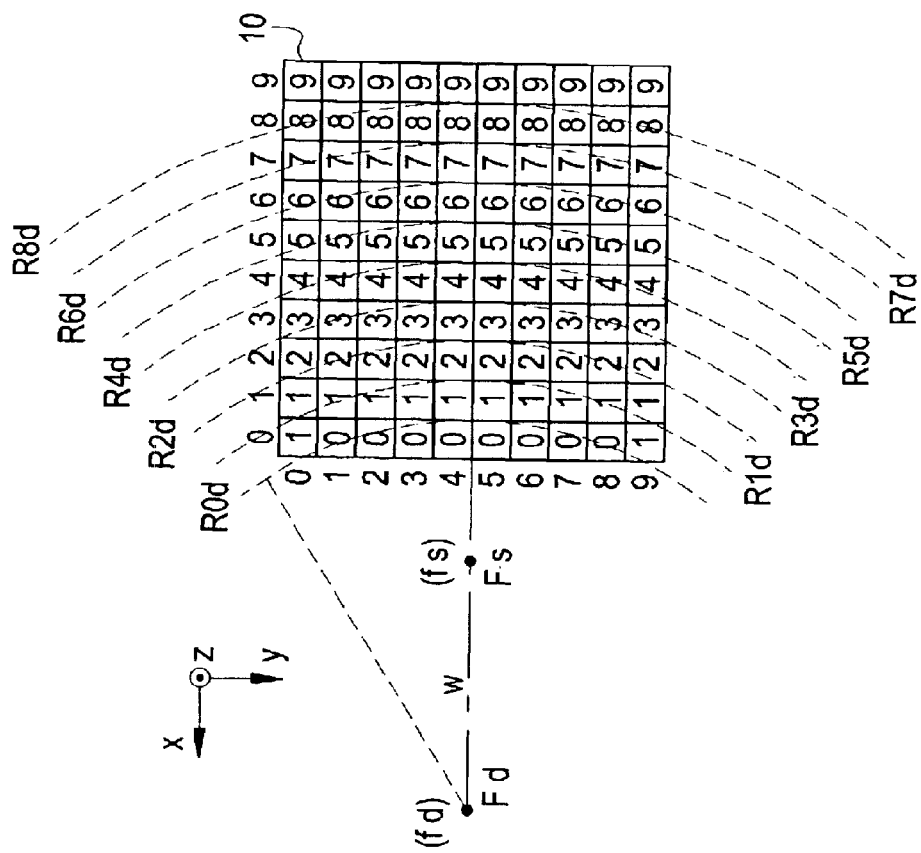
FIG. 16 is an explanatory diagram showing group arrangement of transducers in accordance with the third embodiment.

As shown in FIG. 16(a), the scan controller 7 divides the transducers in the transducer array 10 into groups with group indices "0"–"9", in which transducers lying at the same or approximately the same distance from the shallow imaginary focal spot Fs are in the same group. Next, the scan controller 7 divides the signal voltage e00–e99 into groups with group indices "0"–"9" corresponding to the group arrangement of the transducers, and accordingly divides the current signals i00–i99 into groups with group indices "0"–"9". The matrix switch M is then set so that it adds the current signals in respective groups and outputs the additive current signals I0–I9.

Figure 16B:
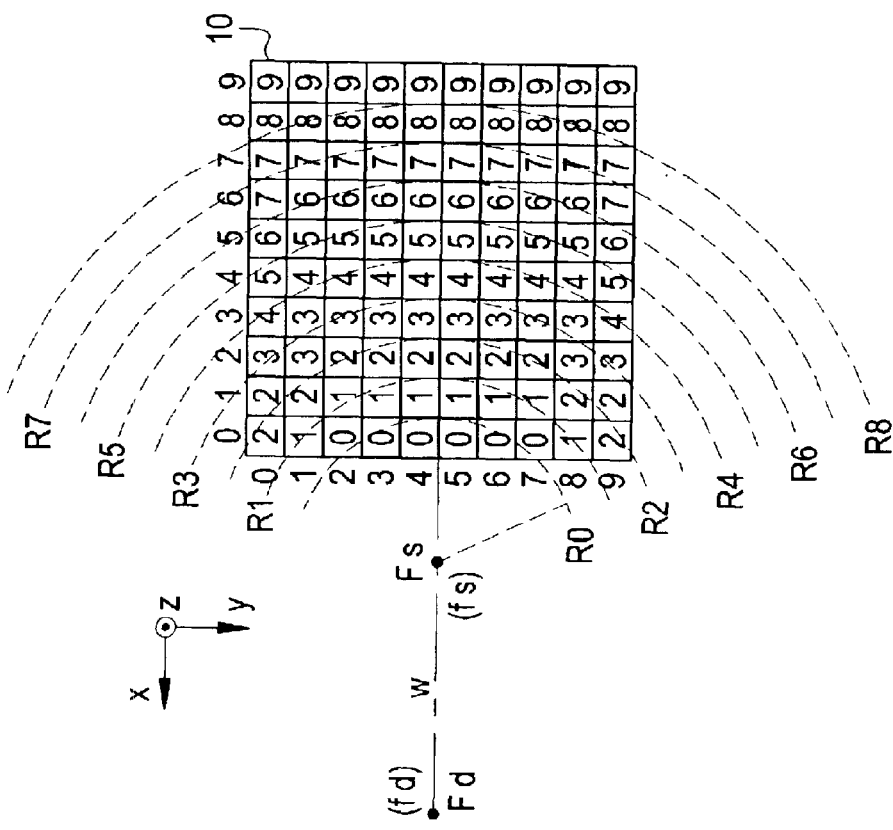

Moreover, as shown in FIG. 16(b), the scan controller 7 divides the transducers in the transducer array 10 into groups with group indices "0"–"9", in which transducers lying at the same or approximately the same distance from the deep imaginary focal spot Fd are in the same group. Next, the scan controller 7 divides the signal voltage e00–e99 into groups with group indices "0"–"9" corresponding to the group arrangement of the transducers, and accordingly divides the current signals i00d–i99d into groups with group indices "0"–"9". The matrix switch Md is then set so that it adds the current signals in respective groups and outputs the additive current signals I0d–I9d.

According to the ultrasonic diagnostic apparatus of the third embodiment, imaging for a shallow region Ps in a scan plane P can be achieved with the output Ws from the digital beamformer unit B and imaging for a deep region Pd can be achieved with the output Wd from the digital beamformer unit Bd, and then, images of these regions Ps and Pd can be smoothly combined.

Fourth Embodiment

Figure 17:
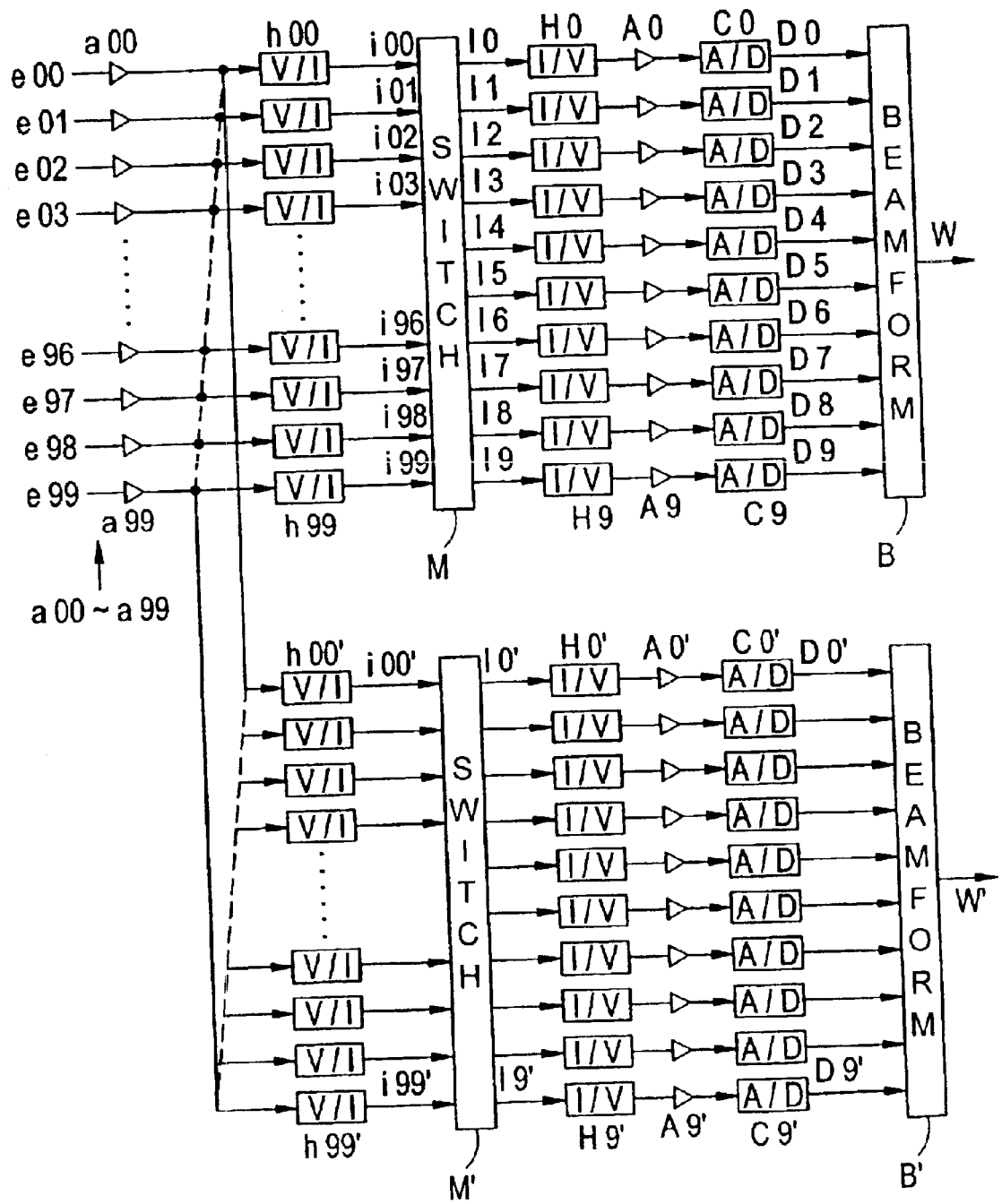
FIG. 17 is a detailed configuration diagram of a receiver section in accordance with a fourth embodiment.

An ultrasonic diagnostic apparatus of the fourth embodiment comprises a receiver section 3-4 shown in FIG. 17 in place of the receiver section 3-1 of FIG. 2.

The receiver section 3-4 includes the configuration of the receiver section 3-1 of FIG. 2 additionally provided with another set of voltage-to-current converters h00'–h99', a matrix switch M', current-to-voltage converters H0'–H9', programmable gain amplifiers A0'–A9', A–D converters C0'–C9', and a digital beamformer unit B'.

Figure 18:
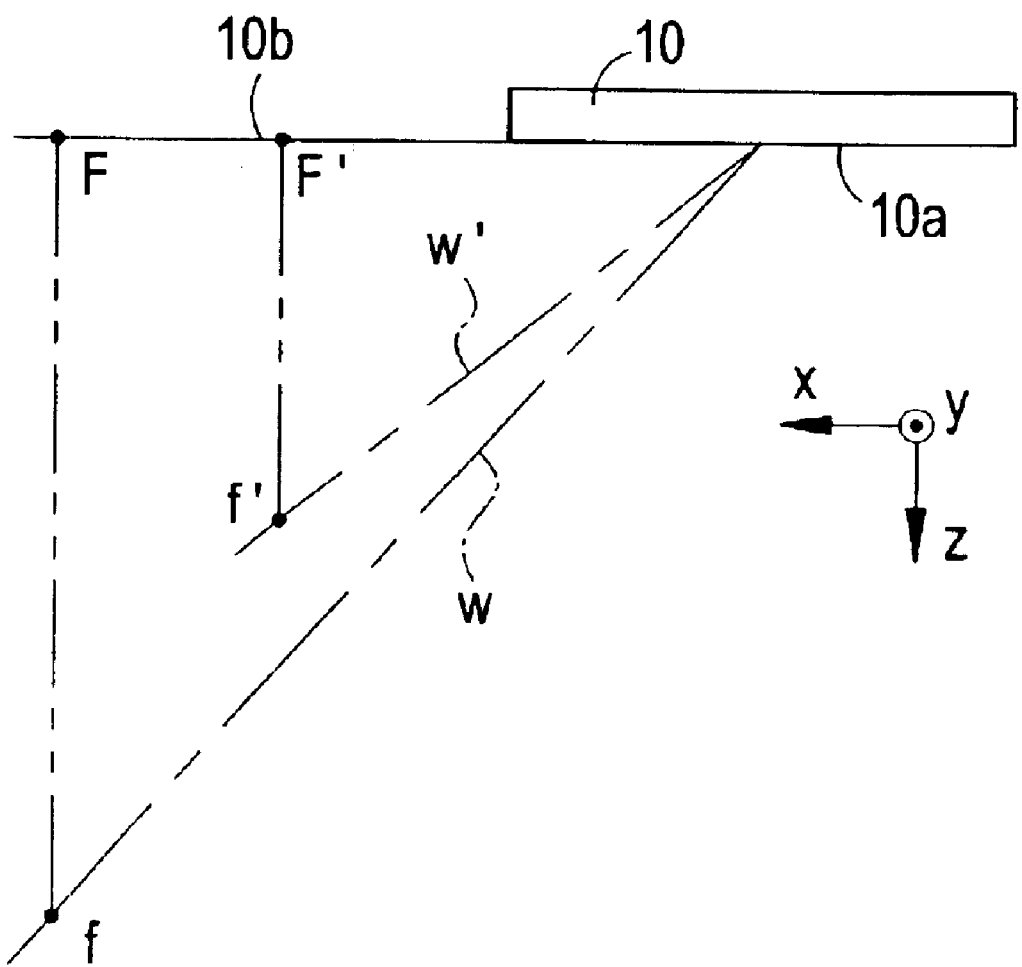
FIG. 18 is an explanatory diagram showing received beams, focal spots and imaginary focal spots in accordance with the fourth embodiment.

As shown in FIG. 18, the digital beamformer unit B and the digital beamformer unit B' form received beams (w, w') in different directions. A first focal spot f of the first received beam (w) formed by the digital beamformer unit B is separate from a second focal spot f' of the second received beam (w') formed by the digital beamformer unit B', and a first imaginary focal spot F and a second imaginary focal spot F' respectively defined by projecting the focal spot f and f onto an imaginary plane 10b do not overlie each other.

Figure 19B:
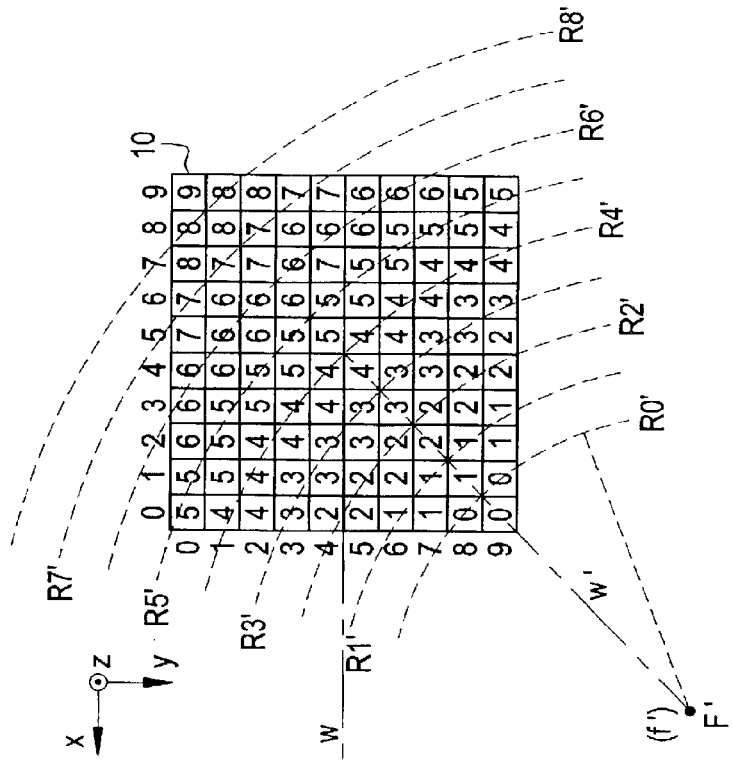
FIG. 19 is an explanatory diagram showing group arrangement of transducers in accordance with the fourth embodiment.
Figure 19A:
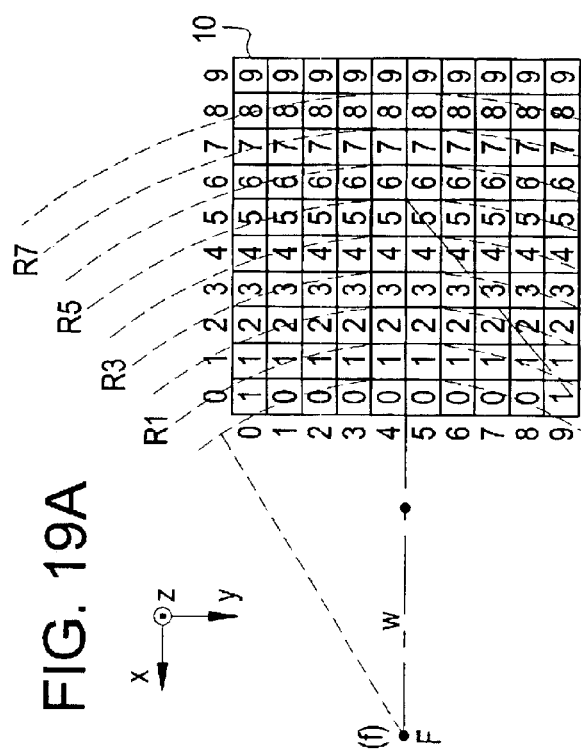

As shown in FIG. 19(a), the scan controller 7 divides the transducers in the transducer array 10 into groups with group indices "0"–"9", in which transducers lying at the same or approximately the same distance from the first imaginary focal spot F are in the same group. Next, the scan controller 7 divides the signal voltage e00–e99 into groups with group indices "0"–"9" corresponding to the group arrangement of the transducers, and accordingly divides the current signals i00–i99 into groups with group indices "0"–"9". The matrix switch M is then set so that it adds the current signals in respective groups and outputs the additive current signals I0–I9.

Moreover, as shown in FIG. 19(b), the scan controller 7 divides the transducers in the transducer array 10 into groups with group indices "0"–"9", in which transducers lying at the same or approximately the same distance from the second imaginary focal spot F' are in the same group. Next, the scan controller 7 divides the signal voltage e00–e99 into groups with group indices "0"–"9" corresponding to the group arrangement of the transducers, and accordingly divides the current signals i00'–i99' into groups with group indices "0"–"9". The matrix switch M is then set so that it adds the current signals in respective groups and outputs the additive current signals I0'–I9'.

According to the ultrasonic diagnostic apparatus of the fourth embodiment, a plurality of separate received beams can be simultaneously formed.

Many widely different embodiments of the invention may be configured without departing from the spirit and the scope of the present invention. It should be understood that the present invention is not limited to the specific embodiments described in the specification, except as defined in the appended claims.

What is claimed is:

1. A method of driving a two-dimensional array ultrasonic probe comprising the steps of:

dividing a first set of N transducers in the two-dimensional array ultrasonic probe into Z (<N) groups, in which a second set of transducers lying at the same or approximately the same distance from a first focal spot of an ultrasonic beam are in the same group;

driving the transducers within the first set on a group-by-group basis; and generating a first set of signals by adding, within a matrix switch, a second set of signals obtained from one of the Z groups of transducers.

2. The method of driving a two-dimensional array ultrasonic probe of claim 1, wherein $4096 \geq N \geq 256$.

3. The method of driving a two-dimensional array ultrasonic probe of claim 1, wherein $128 \geq Z \geq 32$.

4. The method of claim 1 further comprising forming a beam from the second set of signals.

5. The method of claim 1, wherein said generating the first set of signals include adding current signals obtained from the one of the Z groups of transducers.

6. The method of claim 5 further comprising converting voltage signals into the current signals.

7. The method of claim 1 further comprising:

forming a second focal spot lying on an imaginary plane and outside a reception surface of an array including the transducers within the first set by projecting the first focal spot onto the imaginary plane; and grouping the transducers within the first set based on the second focal spot.

* * * * *